US012649037B2

(12) United States Patent
Parker

(10) Patent No.: US 12,649,037 B2
(45) Date of Patent: Jun. 9, 2026

(54) OXYGENATING BITE BLOCK

(71) Applicant: Cedars-Sinai Medical Center, Los Angeles, CA (US)

(72) Inventor: Nathaniel Parker, Mammoth Lakes, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1019 days.

(21) Appl. No.: 17/597,349

(22) PCT Filed: Jul. 14, 2020

(86) PCT No.: PCT/US2020/041969
§ 371 (c)(1),
(2) Date: Jan. 4, 2022

(87) PCT Pub. No.: WO2021/011559
PCT Pub. Date: Jan. 21, 2021

(65) Prior Publication Data
US 2022/0249791 A1 Aug. 11, 2022

Related U.S. Application Data

(60) Provisional application No. 62/875,793, filed on Jul. 18, 2019.

(51) Int. Cl.
*A61M 16/04* (2006.01)
*A61B 1/00* (2006.01)
*A61B 1/01* (2006.01)

(52) U.S. Cl.
CPC ..... *A61M 16/0493* (2014.02); *A61B 1/00135* (2013.01); *A61B 1/01* (2013.01);
(Continued)

(58) Field of Classification Search
CPC .......... A61M 16/0493; A61M 16/0495; A61M 2202/0208; A61M 2202/0225;
(Continued)

(56) References Cited

U.S. PATENT DOCUMENTS

| | | | | | |
|---|---|---|---|---|---|
| 2,127,215 A | * | 8/1938 | Gwathmey | ....... | A61M 16/0488 128/207.14 |
| 5,273,032 A | | 12/1993 | Borody | | |

(Continued)

OTHER PUBLICATIONS

International Search Report and Written Opinion of International Searching Authority for Application No. PCT/US2020/041969, mailed Oct. 1, 2020 (10 pages).

*Primary Examiner* — Timothy A Stanis
*Assistant Examiner* — Matthew R Moon
(74) *Attorney, Agent, or Firm* — Nixon Peabody LLP

(57) ABSTRACT

An endoscopic bite block comprises a base, an elongated guide, and an oxygen inflow tube. The base includes a body and a central passageway extending through the body. The central passageway is configured to receive an endoscope. The elongated guide includes a longitudinal curvature corresponding in shape to an oral-pharyngeal cavity of a patient. The elongated guide extends from the base and toward a retropharyngeal space of the patient. The elongated guide includes a lateral curvature for guiding the endoscope along the longitudinal curvature of the elongated guide. The oxygen inflow tube is configured to receive oxygen gas from an oxygen source. The oxygen inflow tube extends from the base along the elongated guide such that the oxygen inflow tube is configured to deliver the received oxygen gas to the retropharyngeal space of the patient.

25 Claims, 8 Drawing Sheets

(52) U.S. Cl.
CPC . *A61M 16/0495* (2014.02); *A61M 2202/0208*
(2013.01); *A61M 2209/088* (2013.01)

(58) Field of Classification Search
CPC ........ A61M 2209/088; A61M 2209/06; A61M
2210/0625; A61M 2230/432; A61B
1/00135; A61B 1/00154; A61B 1/01;
A61B 1/24; A61B 90/16; A61C 17/08;
A61C 5/82; A61C 5/90
See application file for complete search history.

(56) References Cited

U.S. PATENT DOCUMENTS

| | | | |
|---|---|---|---|
| 7,624,736 B2 | 12/2009 | Borody | |
| 8,028,704 B2 | 10/2011 | Reynolds, II et al. | |
| 8,555,886 B2 | 10/2013 | Coleman et al. | |
| 10,029,060 B2 * | 7/2018 | McCauley | A61B 5/0836 |
| 2004/0129272 A1 | 7/2004 | Ganesh | |
| 2009/0013995 A1 | 1/2009 | Williams | |
| 2010/0030027 A1 | 2/2010 | Bastid et al. | |
| 2010/0101567 A1 * | 4/2010 | Hauge | A61M 16/0495 128/200.26 |
| 2011/0180065 A1 * | 7/2011 | Hajgato | A61M 16/0488 128/200.26 |
| 2012/0143003 A1 * | 6/2012 | Anca | A61M 16/0497 600/114 |
| 2014/0007868 A1 | 1/2014 | Eaton et al. | |
| 2014/0209095 A1 | 7/2014 | Anca et al. | |
| 2015/0265792 A1 * | 9/2015 | Goudra | A61B 1/00154 600/114 |
| 2016/0045699 A1 * | 2/2016 | Cardillo | A61B 1/01 600/120 |
| 2020/0029800 A1 * | 1/2020 | Matus | A61B 1/00147 |
| 2022/0304561 A1 * | 9/2022 | Sumiyama | A61B 1/01 |

* cited by examiner

700

730

760

750

716

718

710

712

735

OXYGENATING BITE BLOCK

CROSS-REFERENCE TO RELATED APPLICATIONS

This application is the National Phase of International Application PCT/US2020/041969, filed Jul. 14, 2020, which designated the United States, which claims priority to and the benefit of U.S. Provisional Patent Application No. 62/895,793, filed on Jul. 18, 2019, each of which is hereby incorporated by reference herein in its entirety.

TECHNICAL FIELD

This disclosure relates to a bite block for use in an endoscopic procedure, and more specifically, to a bite block that provides oxygenation in a retropharyngeal space of a patient.

BACKGROUND

Cardiologists, anesthesiologists, and gastroenterologists often use bite blocks to protect patients' teeth and to facilitate scoping during sedated diagnostic procedures, such as in an esophagogastroduodenoscopy (EGD) and a trans-esophageal echocardiography (TEE). These procedures are normally performed using various intravenous sedation technique(s) and require supplemental oxygenation.

SUMMARY

Typically, due to the sedation required for comfortable placement of an endoscope or TEE scope, oxygenation can be facilitated using a nasal cannula or a cut mask. These methods of oxygenation can result in increased dead space ventilation and inefficient oxygen supplementation. However, as an example, many patients undergoing TEE are quite sick and need as efficient oxygen delivery to their lungs as possible. Thus, a need exists for an oxygenating bite block that reduces a patient's airway dead space and/or improves ventilation.

The present disclosure is directed to solving these problems and addressing other needs. For example, the present disclosure eliminates the need for two devices (e.g., an oxygen delivery device and a bite block) and improves on the oxygen delivery efficiency. Furthermore, the present disclosure provides for easier placement of the oxygen tubes and the scope down towards the esophagus during an EGD or a TEE. Additionally, the present disclosure can be implemented during other procedures, such as advanced upper endoscopy, esophagogastroduodenoscopy, endoscopy, EGD included EUS, endoscopic ultrasoundography and ERCP, endoscopic retrograde cholangiopancreatography, and the like. The present disclosure may also decrease the incidence of sore throat following the performance of a difficult to place EGD or TEE probe by protecting the retropharyngeal soft tissue from trauma.

Thus, the present disclosure relates to a bite block that is improved to provide oxygenation in the retropharyngeal space (e.g., close to the glottic opening) which reduces airway dead space. The bite block keeps the patient's mouth open to prevent injury during an endoscopic procedure (e.g., EGD or TEE), while simultaneously providing oxygen to the patient's airway.

According to some implementations of the present disclosure, an endoscopic bite block comprises a base, an elongated guide, and an oxygen inflow tube. The base includes a body and a central passageway extending through the body. The central passageway is configured to receive an endoscope. The elongated guide includes a longitudinal curvature corresponding in shape to an oral-pharyngeal cavity of a patient. The elongated guide extends from the base and toward a retropharyngeal space of the patient. The elongated guide includes a lateral curvature for guiding the endoscope along the longitudinal curvature of the elongated guide. The oxygen inflow tube is configured to receive oxygen gas from an oxygen source. The oxygen inflow tube extends from the base along the elongated guide such that the oxygen inflow tube is configured to deliver the received oxygen gas to the retropharyngeal space of the patient.

In some examples, the endoscopic bite block further comprises a flange at an end of the base opposite the elongated guide. The flange is dimensioned to preclude the device from entering the oral cavity of the patient. In some examples, the base includes a recess and/or padded surface configured to engage upper and lower teeth of the patient during an endoscopic procedure. In some examples, the endoscopic bite block further comprises a detachable elastic headband for holding the base in place relative to the oral cavity of the patient.

In some examples, the elongated guide is configured to depress a tongue of the patient upon insertion, thereby displacing an epiglottis away from a posterior pharyngeal wall of the patient. In some examples, the elongated guide includes a flexible distal portion configured to flex in an anterior direction as the flexible distal portion abuts pharynx tissue of the patient.

In some examples, the oxygen inflow tube is integral to the elongated guide, such that the oxygen inflow tube follows the longitudinal curvature of the elongated guide. In some such examples, the elongated guide is further configured to guide the oxygen inflow tube to the retropharyngeal space of the patient. In some examples, the elongated guide and the oxygen inflow tube are integral to the base of the bite block.

In some examples, the elongated guide is further configured to guide the endoscope along a first side of the elongated guide, and the oxygen inflow tube is configured to extend along a second side of the elongated guide opposite the first side of the elongated guide.

In some examples, the endoscopic bite block further comprises a second oxygen inflow tube, wherein the first and second oxygen inflow tubes are integral to the elongated guide. Additionally, or alternatively, the endoscopic bite block further comprises an end-tidal carbon dioxide return tube for monitoring carbon dioxide in respiratory gases of the patient.

According to some implementations of the present disclosure, an endoscopic bite block comprises a base, an elongated guide, and an oxygen inflow tube. The base includes a recess configured to engage upper and lower teeth of a patient. The base has a body and a central passageway extending through the body. The central passageway is configured to receive an endoscope. The elongated guide having a longitudinal curvature corresponding in shape to an oral-pharyngeal cavity of the patient. The elongated guide extends from the base and toward a retropharyngeal space of the patient. The elongated guide has a lateral curvature for guiding the endoscope along the longitudinal curvature of the elongated guide. The oxygen inflow tube is integral to the elongated guide and is configured to receive oxygen gas from an oxygen source. The oxygen inflow tube extends from the base along the longitudinal curvature of the elongated guide, such that the oxygen inflow tube is configured to deliver the received oxygen gas to the retropharyngeal space of the patient.

According to some implementations of the present disclosure, an endoscopic bite block kit includes an endoscopic bite block and a gas tube. The endoscopic bite block includes a base, an elongated guide, and an oxygen inflow tube. the base includes a body and a central passageway extending through the body. The body includes a recess configured to engage upper and lower teeth of a patient. The central passageway is configured to receive an endoscope. The elongated guide includes a longitudinal curvature corresponding in shape to an oral-pharyngeal cavity of the patient. The elongated guide extends from the base and toward a retropharyngeal space of the patient. The elongated guide includes lateral curvature for guiding the endoscope along the longitudinal curvature of the elongated guide The oxygen inflow tube is integral to the elongated guide and is configured to receive oxygen gas from an oxygen source. The oxygen inflow tube extends from the base along the longitudinal curvature of the elongated guide, such that the oxygen inflow tube is configured to deliver the received oxygen gas to the retropharyngeal space of the patient. The gas tube is configured to couple to the oxygen inflow tube of the endoscopic bite block at a first end of the gas tube. The gas tube is further configured to couple to the oxygen source at a second end of the gas tube.

In some examples, the endoscopic bite block of the kit is disposable. In some examples, the endoscopic bite block kit further includes an elastic headband for holding the base of the endoscopic bite block in place relative to the oral cavity of the patient. The elastic headband configured to attach to the endoscopic bite block.

According to some implementations of the present disclosure, an endoscopic bite block comprises a base, an oxygen inflow tube protruding from the base, and an elongated guide protruding from the base. The base includes a body and a flange. The body is configured to be encapsulated by lips of a patient thereby keeping a mouth of the patient open during a medical procedure. The flange is dimensioned to preclude the flange from entering an oral cavity of the patient. The oxygen inflow tube is configured to receive oxygen gas from an oxygen source. The elongated guide is configured to guide the oxygen inflow tube to a retropharyngeal space of the patient. The oxygen inflow tube protrudes from the base in a same direction as the elongated guide. The oxygen inflow tube is configured to supply the received oxygen gas to the retropharyngeal space of the patient. The elongated guide includes a lateral curvature for guiding a medical device (e.g., an endoscope), thereby protecting a throat passageway of the patient.

In some examples, the oxygen inflow tube protrudes from the base in a same longitudinal curvature as the elongated guide.

In some examples, the elongated guide is configured to slide a distance relative to the base of the bite block. In some such examples, the distance is between two to five centimeters. The base further includes a central passageway extending through the body. The central passageway is configured to receive an endoscope. The elongated guide further includes an attachment at an end proximate the base. The attachment is dimensioned to preclude the end of the elongated guide from entering the central passageway.

The foregoing and additional aspects and implementations of the present disclosure will be apparent to those of ordinary skill in the art in view of the detailed description of various embodiments and/or implementations, which is made with reference to the drawings, a brief description of which is provided next.

BRIEF DESCRIPTION OF THE DRAWINGS

The foregoing and other advantages of the present disclosure will become apparent upon reading the following detailed description and upon reference to the drawings.

Figure 1:
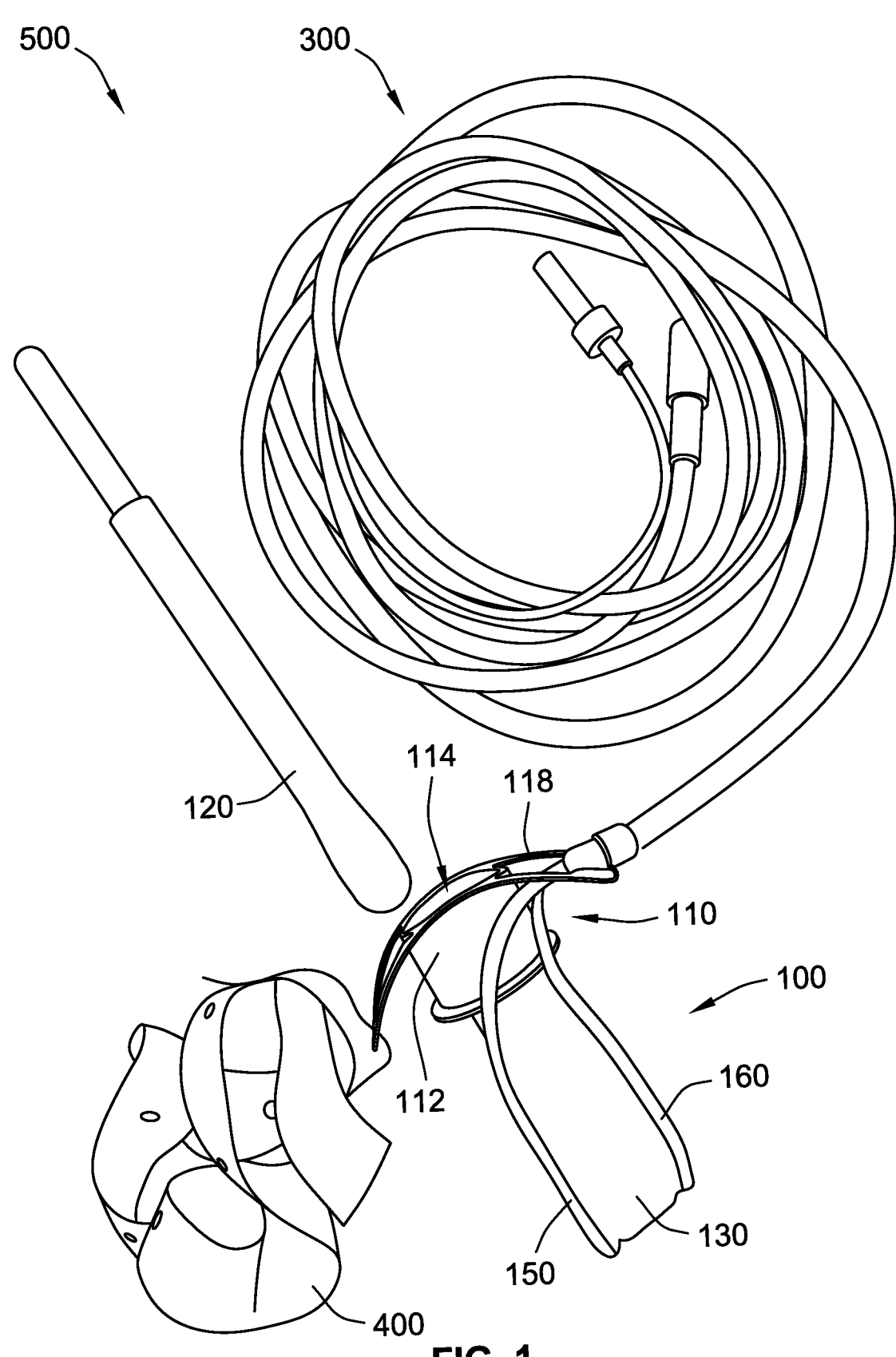
FIG. 1 illustrates an endoscopic bite block kit, according to some implementations of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present invention is described with reference to the attached figures, where like reference numerals are used throughout the figures to designate similar or equivalent elements. The figures are not drawn to scale, and are provided merely to illustrate the instant invention.

The present disclosure is directed to a device having a bite block and oxygenation delivery tubes. More specifically, and as described below, the device includes (a) a bite block having a plastic flange that is configured to be encapsulated by a patient's lips, thereby keeping the patient's mouth open during a medical procedure, (b) a curved elongated guide protruding from the bite block that is configured to guide oxygen tubes to a retropharyngeal space, and (c) oxygen tubes that protrude from the bite block in a same direction (and/or same longitudinal curvature) as the elongated guide, wherein the oxygen tubes are configured to supply air to the patient's retropharyngeal space, and wherein the elongated guide includes a lateral curvature for guiding a separate medical device (e.g., endoscope, fiberoptic scope), thereby protecting the patient's throat passageway.

Thus, the present disclosure serves at least three main purposes: (1) to protect the patient's teeth and tongue, the endoscopic device, and the physician's hand with the bite block; (2) to reduce dead space and provide oxygenation in the retropharyngeal space with the oxygen tubes; and (3) to facilitate scoping during an endoscopic procedure using the longitudinal and lateral curvatures of the elongated guide.

Figure 2:
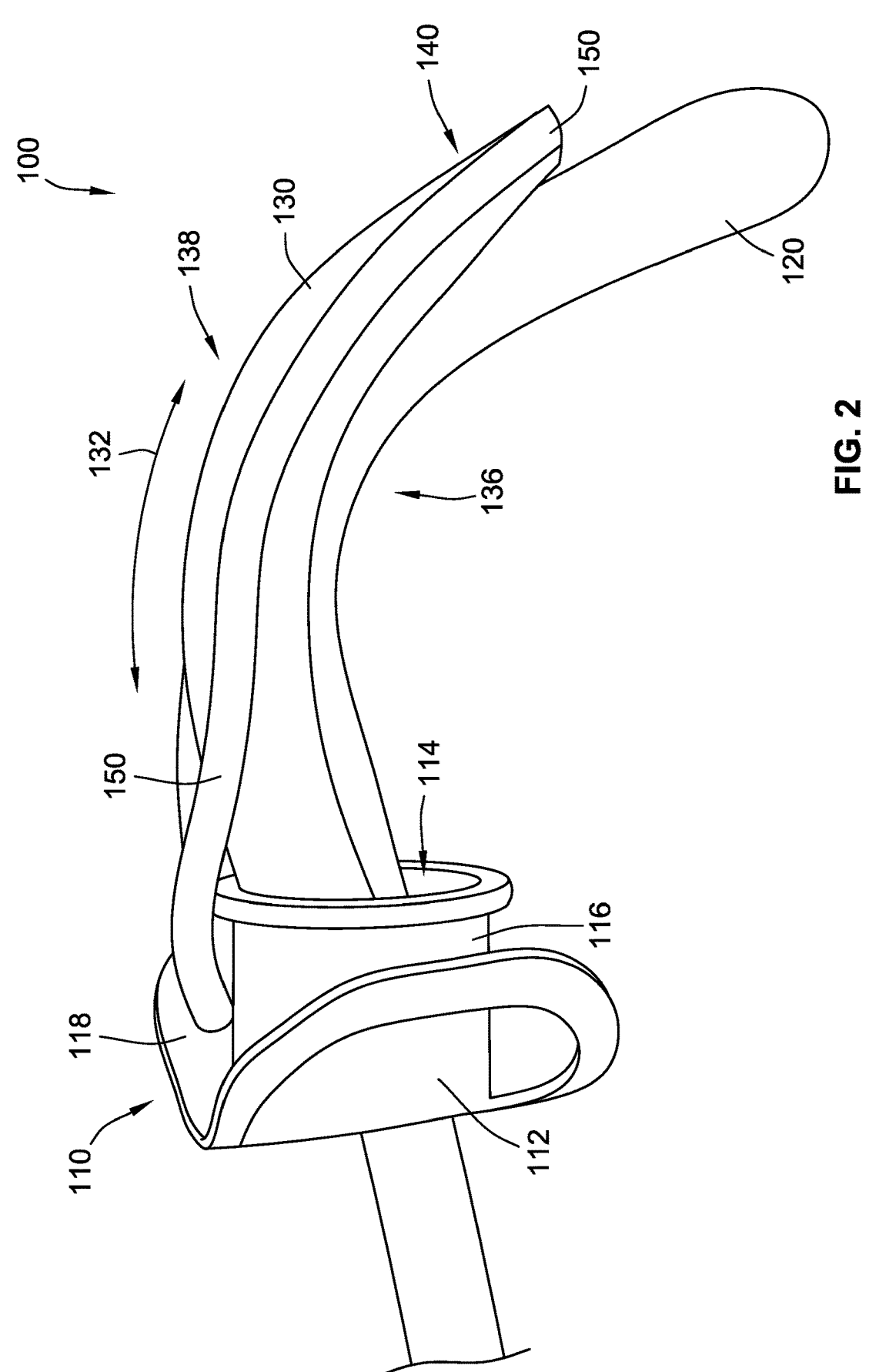
FIG. 2 illustrates a side view of an endoscopic bite block and an endoscope of the endoscopic bite block kit of FIG. 1, according to some implementations of the present disclosure.

Referring generally to FIGS. 1-2, an exemplary endoscopic bite block kit 500 includes a bite block 100, a gas tube 300, and an elastic headband 400. The bite block 100 includes a base 110, an elongated guide 130 (e.g., elongated sliding guide) integral to the base 110, an oxygen inflow tube 150, and a secondary tube 160. Optionally, the exemplary bite block 100 includes the elastic headband 400 for holding the base 110 in place relative to the oral cavity of an patient 20. Alternatively, the elastic headband 400 is separate from the bite block 100, and is configured to be attached to the bite block 100 prior to use.

Figure 3:
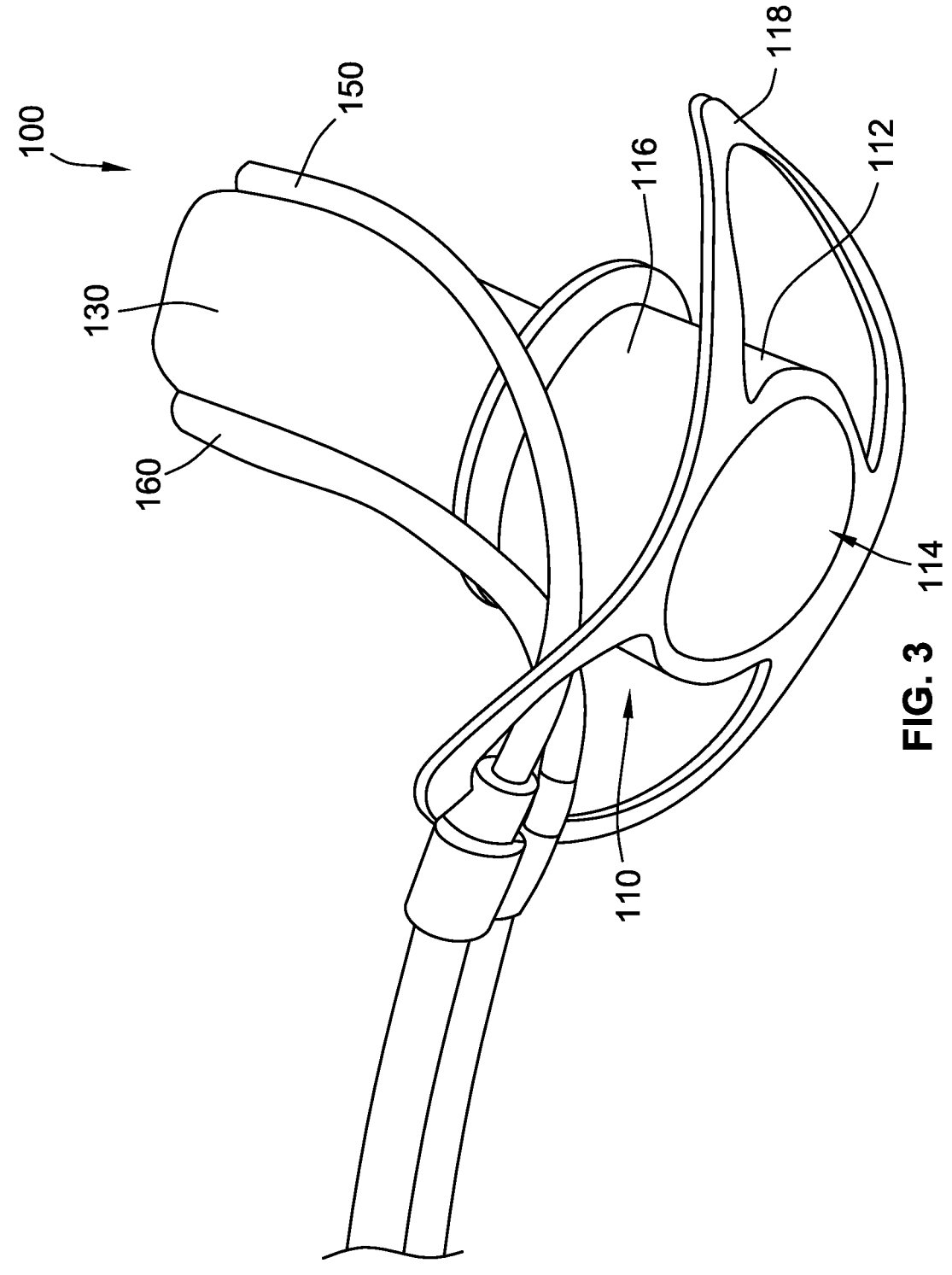
FIG. 3 illustrates a top perspective view of the endoscopic bite block of FIG. 2, according to some implementations of the present disclosure.

As best shown in FIGS. 2-3, the base 110 includes a body 112, and a central passageway 114 extending through the body 112 (e.g., extending between the teeth and into the mouth). The body 112 is configured to be encapsulated by lips of the patient 20, thereby keeping mouth of the patient 20 open during a medical procedure (e.g., esophagogastroduodenoscopy (EGD) or transesophageal echocardiography (TEE)). The central passageway 114 is configured to receive an endoscope 120. The body 112 of the base 110 includes a recess 116 configured to engage upper and lower teeth of the patient 20 during an endoscopic procedure. In addition, or as an alternative to having the recess 116, the body 112 of the base 110 includes a flange 118 at an end of the base 110 opposite the elongated guide 130. The flange 118 is dimensioned to preclude the end of the base 110 and the flange 118 from entering the oral cavity of the patient 20.

Figure 6:
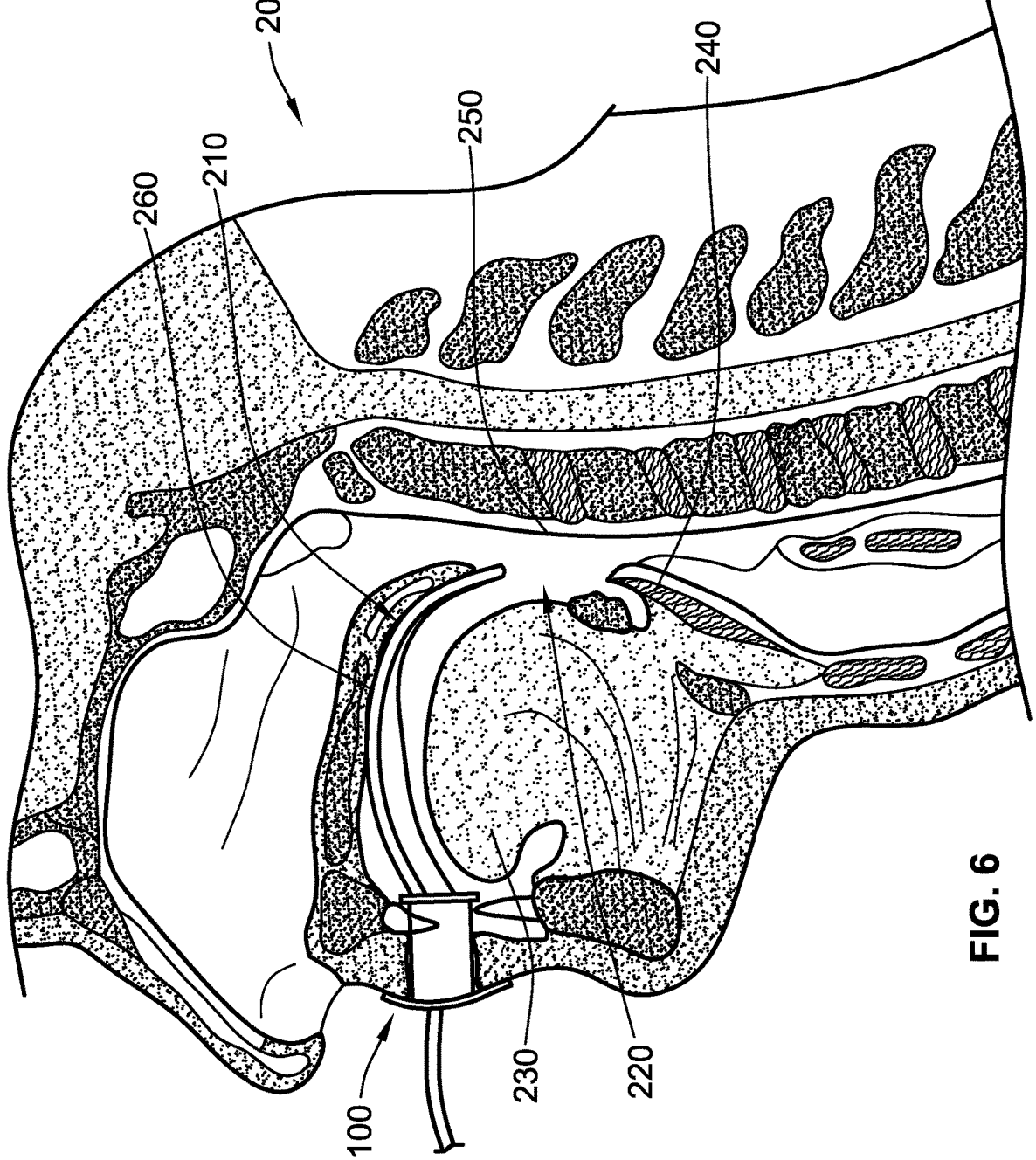
FIG. 6 illustrates an upper airway of a patient receiving the endoscopic bite block of FIG. 2, according to some implementations of the present disclosure.

The elongated guide 130 includes a longitudinal curvature 132 corresponding in shape to an oral-pharyngeal cavity 210 of a patient 20. As best shown in FIG. 6, the elongated guide 130 extends from the base 110 and toward a retropharyngeal space 220 of the patient 20. The elongated guide 130 includes a flexible distal portion 140 configured to flex in an anterior direction as the flexible distal portion 140 abuts pharynx tissue 260 of the patient 20. The elongated guide 130 also includes a second portion that is more rigid than the flexible distal portion 140, such that the elongated guide 130 is configured to depress a tongue 230 of the patient 20 upon insertion, thereby displacing an epiglottis 240 away from a posterior pharyngeal wall 250 of the patient 20.

Figure 4:
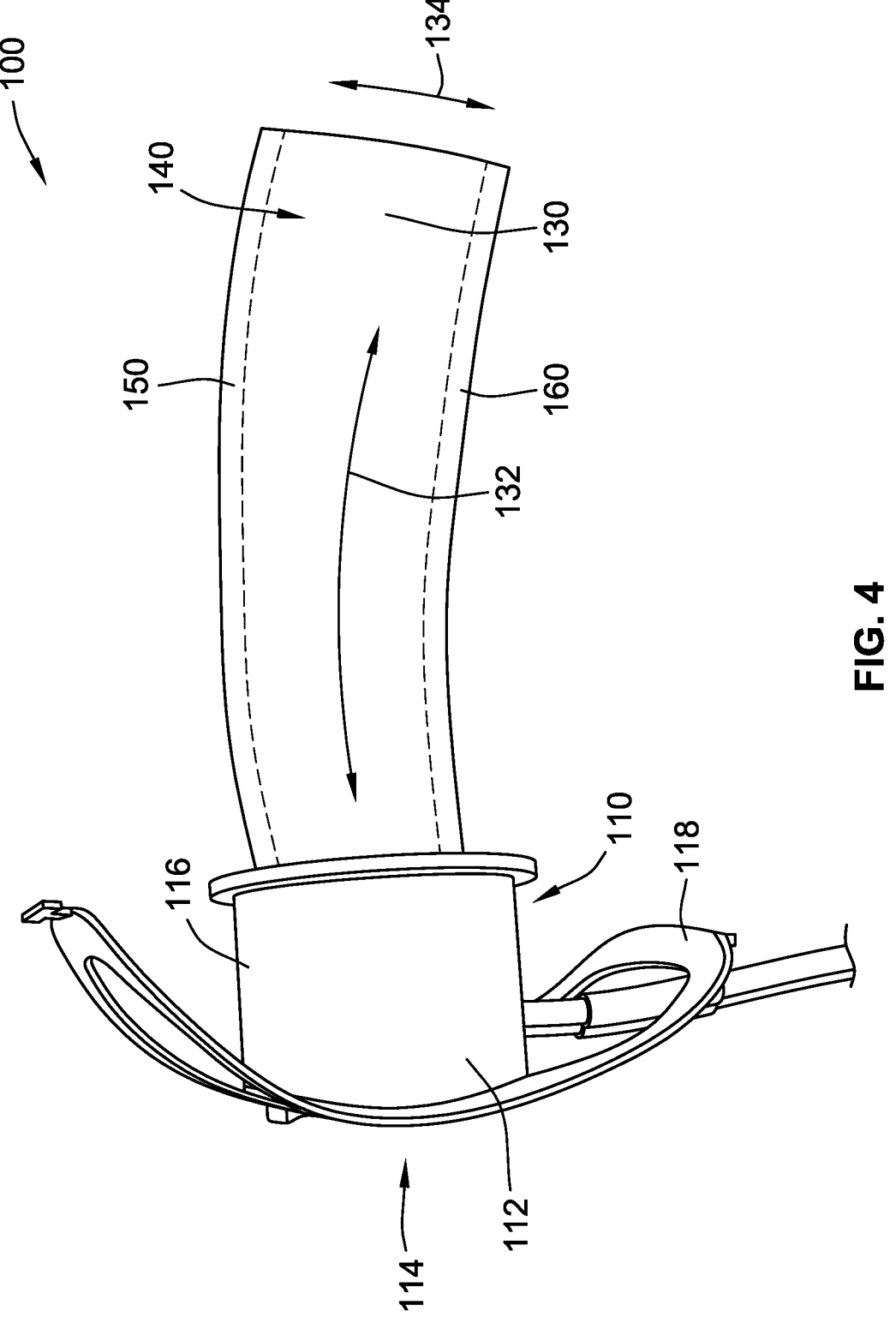
FIG. 4 illustrates a bottom view of the endoscopic bite block of FIG. 2, according to some implementations of the present disclosure.
Figure 5:
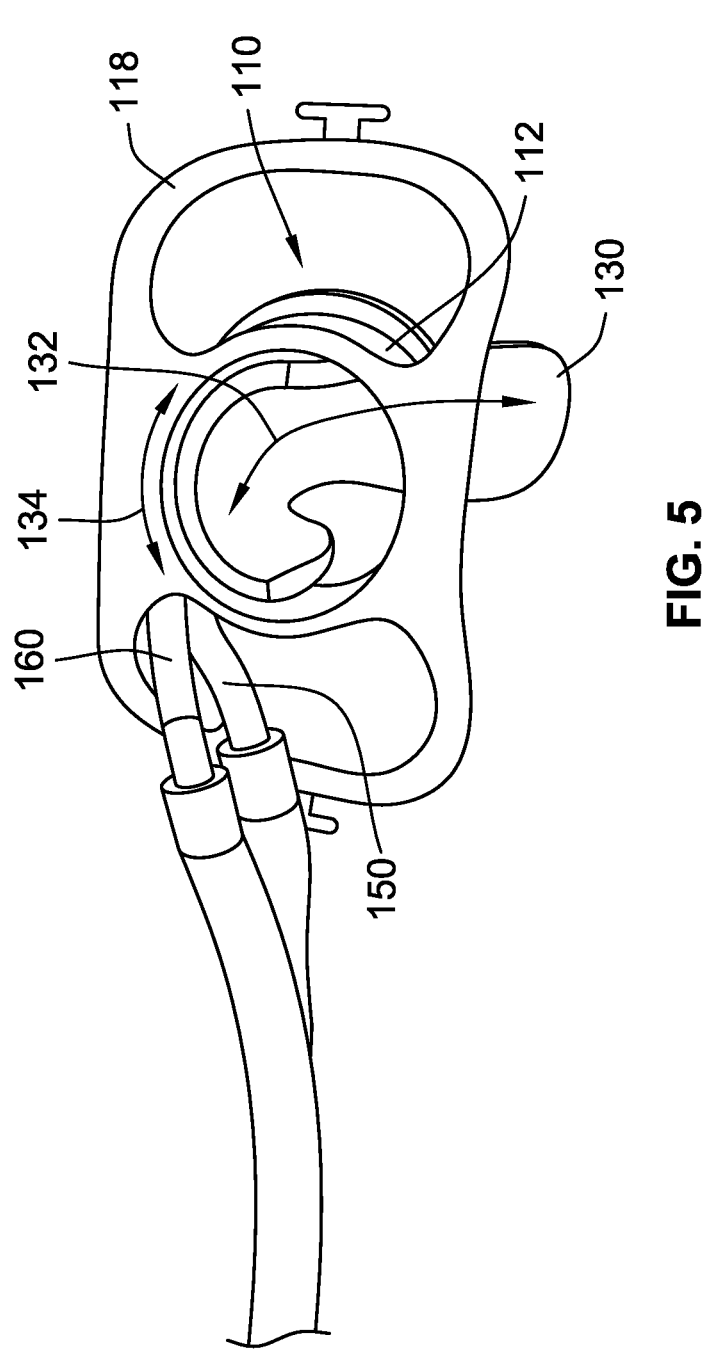
FIG. 5 illustrates a front perspective view of the endoscopic bite block of FIG. 2, according to some implementations of the present disclosure.

Referring now to FIGS. 4-5, the elongated guide 130 has a lateral curvature 134 for guiding the endoscope 120 along the longitudinal curvature 132 of the elongated guide 130, thereby protecting a throat passageway of the patient 20 from trauma that may be caused by the endoscope 120. As such, the elongated guide 130 is further configured to guide the oxygen inflow tube 150 to a retropharyngeal space 220 of the patient 20. Therefore, the elongated guide 130 not only guides the oxygen back, but also assists the proceduralist in the placement of the endoscope 120 down towards the esophagus. In some examples, the concavity (e.g., longitudinal curvature 132) of the elongated guide 130 is altered based on patient anatomy, patient experience, or the like. In some examples, the shape of the elongated guide 130 is based on (e.g., corresponding to, parallel to, mirroring) various curvatures associated with the hard palates of patients. The variances in degree of palatine curve can be mitigated by offering a variety of sizes of the bite block (such as the exemplary bite block 100) wherein people with lower arches could use a bite block with a smaller sized elongated guide (e.g., a bite block designed for a smaller person) that is still big enough to accommodate an endoscope or a TEE probe.

The oxygen inflow tube 150 is configured to receive oxygen gas from an oxygen source. The oxygen inflow tube 150 can be attached to tank or wall oxygen in a usual fashion (not shown). The oxygen inflow tube 150 extends from the base 110 along the elongated guide 130, such that the oxygen inflow tube 150 is configured to deliver the received oxygen gas to the retropharyngeal space 220 of the patient 20. In some examples, the oxygen inflow tube 150 is integral to the elongated guide 130 such that the oxygen inflow tube 150 follows the longitudinal curvature 132 of the elongated guide 130. With the shape of the elongated guide 130 and the placement of the oxygen inflow tube 150, and particularly in combination of both, the bite block 100 helps reduce airway dead space ventilation, which will in turn improve oxygenation of the patient 20 who receives the endoscopic procedure, especially when compared to using a traditional nasal cannula. As such, the bite block 100 delivers oxygen via the oxygen inflow tube 150 further back into the retropharynx and closer to the glottis opening.

The elongated guide 130 includes a first side 136, and a second side 138 opposite the first side 136. The first side 136 is configured to contact the tongue 230 of the patient 20. The second side 138 is configured to contact palate tissue of the patient 20. In some examples, the second side 138 is configured to contact the hard palate tissue of the patient 20, including where hard palate joins the soft palate along the palatine raphe of the patient. While the elongated guide 130 is configured to guide the endoscope 120 along the first side 136 of the elongated guide 130, the oxygen inflow tube 150 and the secondary tube 160 are configured to extend along the second side 138 of the elongated guide 130. While the exemplary bite block 100 includes the tubes 150, 160 on the opposite side of the elongated guide 130 from where the endoscope 120 is inserted, it is also contemplated that the oxygen inflow tube 150 (and/or the secondary tube 160) is located on the first side 136 of the elongated guide 130, so long as the oxygen inflow tube 150 is positioned to provide unencumbered movement of the endoscope 120.

Similar to the oxygen inflow tube 150, the secondary tube 160 extends from the base 110 along the elongated guide 130 and is integral to the elongated guide 130. Thus, secondary tube 160 follows the longitudinal curvature 132 of the elongated guide 130. In some examples, the secondary tube 160 is a second oxygen inflow tube that is the same as, or similar to, the oxygen inflow tube 150. In some other examples, the secondary tube 160 is an end-tidal carbon dioxide return tube 160 for monitoring carbon dioxide in respiratory gases of the patient 20. While a tubing arrangement of the bite block 100 is shown to have an oxygen inflow tube 150 and a secondary tube 160, more or fewer tubes are also contemplated. For example: a first alternative tubing arrangement includes only an oxygen inflow tube; a second alternative tubing arrangement includes a first oxygen inflow tube, a second oxygen inflow tube, and an end-tidal carbon dioxide return tube.

It is contemplated that the bite block 100 may come in a variety of sizes dependent on, for example, intended scope size and patient size. It is also contemplated that the bite block 100 is manufactured with a 3D printer, and/or disposable after use. According to some implementations of the present disclosure, the oxygen inflow tube 150 and the secondary tube 160 are integrated to the elongated guide 130. Therefore, the entire bite block 100 (including the base 110, the elongated guide 130, the oxygen inflow tube 150, and the secondary tube 160) can be manufactured as one single piece. According to some other implementations of the present disclosure, the oxygen inflow tube 150 and the secondary tube 160 are manufactured separately from the elongated guide 130. Therefore, the base 110 and the elongated guide 130 are manufactured as one piece; the oxygen inflow tube 150 and the secondary tube 160 can be attached to or integrated to the base 110 and/or the elongated guide 130 during assembly of the bite block 100.

While the bite block 100 is shown in FIGS. 1-5 as including a base 110, a body 112, a central passageway 114, a recess 116, a flange 118, an elongated guide 130, an oxygen inflow tube 150, and a secondary tube 160, alternative bite blocks that are the same as, or similar to, the bite block 100 can be construed with more or fewer components. For example, a first alternative bite block (not shown) includes a base 110, a body 112, a central passageway 114, a flange 118, an elongated guide 130, an oxygen inflow tube 150, and a secondary tube 160 (e.g., no recess 116).

Referring back to FIG. 1, the exemplary endoscopic bite block kit 500 includes the bite block 100, the gas tube 300, and the elastic headband 400. In some examples, the bite block 100 of the endoscopic bite block kit 500 is the same as, or similar to, the bite block 100 as shown in FIGS. 2-6. In some other examples, the endoscopic bite block kit 500 includes alternative embodiments of the bite block 100, such as the ones described herein.

According to some implementations of the present disclosure, the gas tube 300 is configured to couple to an oxygen inflow tube 150 of the bite block 100 at a first end of the gas tube 300 and configured to couple to an oxygen source at a second end of the gas tube 300. The elastic headband 400 is configured to attach to the bite block 100, and to hold a base 110 of the bite block 100 in place relative to the oral cavity of the patient 20.

Therefore, the present disclosure provides for easier placement of the oxygen inflow tube 150 and the scope 120 down towards the esophagus of the patient 20 during an EGD or a TEE. As such, the bite block 100 helps (1) increase ventilation of the patient's airway, and (2) decrease the incidence of sore throat following the performance of a difficult to place EGD or TEE probe by protecting the retropharyngeal soft tissue from trauma.

It is also noted that some patients have extremely sensitive gag reflexes that will not permit an entirety of the bite block 100 to be placed prior to sedation. For example, patients who receive oxygen prior to sedation typically have a bite block placed prior to sedation as well, because patients may bite down while being sedated and the mouth cannot then be opened to accommodate a scope or a bite block. As such, another alternative bite block, such as the bite block 700 shown in FIGS. 7A and 7B, includes an elongated guide 730 having an oxygen inflow tube 750 and a secondary tube 760. The bite block 700 is the same as, or similar to, the bite block 100, where like reference numbers are used for like elements, except that the body 712 is separate from the elongated guide 730.

Figure 7A:
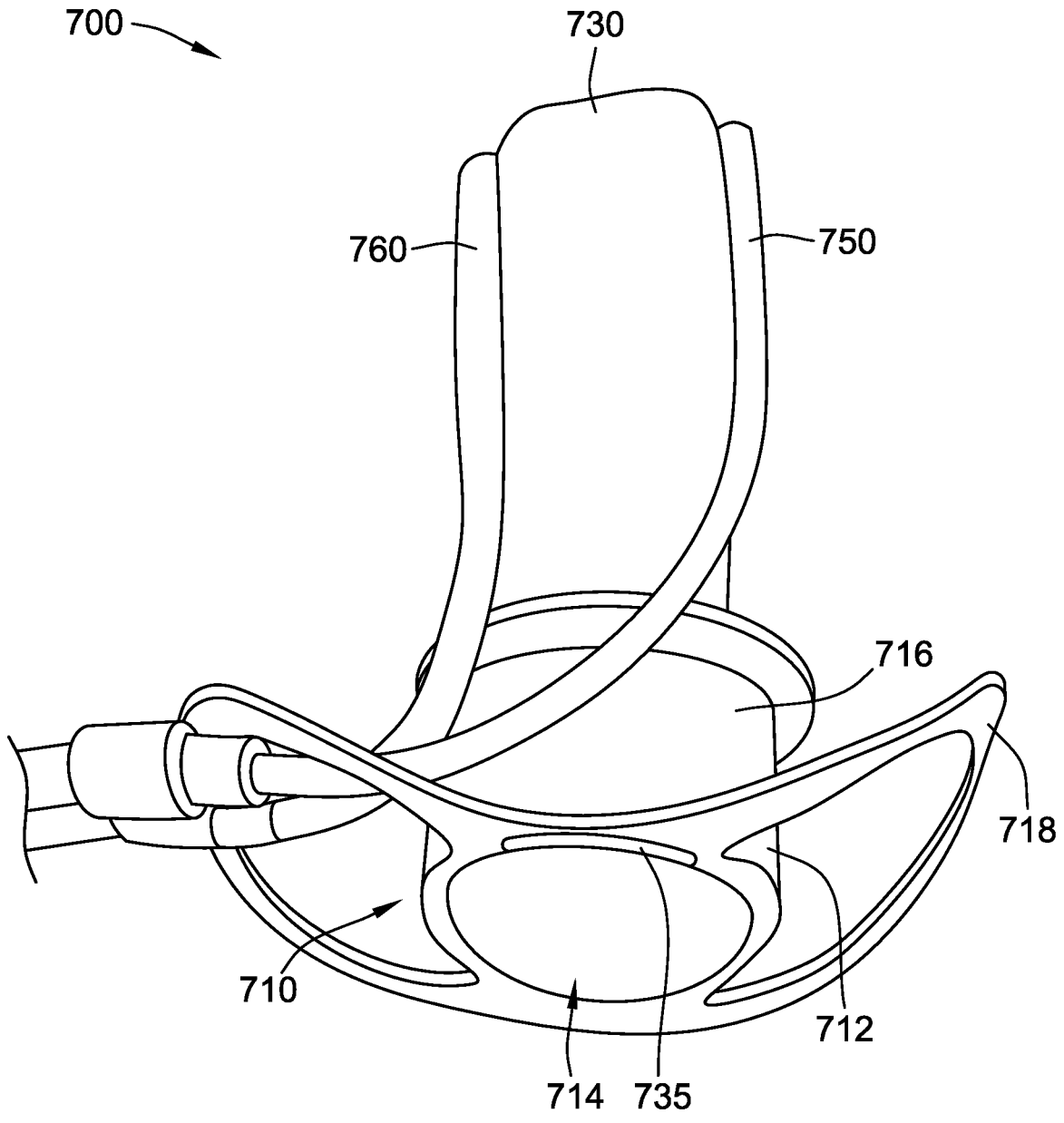
FIG. 7A illustrates a top perspective view of an endoscopic bite block in a first configuration, according to some implementations of the present disclosure.
Figure 7B:
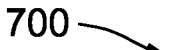
FIG. 7B illustrates a top perspective view of the endoscopic bite block of FIG. 7A in a second configuration, according to some implementations of the present disclosure.

The elongated guide 730 is configured to slide relative to the body 712 from a first configuration (FIG. 7A) to a second configuration (FIG. 7B). For example, the elongated guide 730 is configured to slide two to five centimeters from an opening of the central passageway 714 after the patient is pre-oxygenated, such that the elongated guide 730 does not trigger too much gag reflex for having the elongated guide 730 (e.g., the flexible distal portion of the elongated guide 730) too far back while the patient is not sedated. For example, in some implementations, the movable (e.g., slidable) elongated guide 730 can improve patient comfort upon placement and decrease intolerance in gag sensitive patients.

In some implementations, the elongated guide 730 (e.g., the sliding guide) can snap into place at, for example, various increments at 3 mm-8 mm intervals to secure the sliding guide in an appropriate position for a particular individual. This ensures a custom fit according to the depth of the individual's mouth. Additionally or alternatively, in some implementations, the sliding guide can be free to slide in its channel when the scope is initially placed to facilitate placement, then secured once the scope is down the esophagus (e.g., incrementally).

After sliding into a desired location from the opening of the central passageway 714, the elongated guide 730 is configured to snap into place with an attachment groove 735 around the anterior portion (e.g., the portion proximate the body 712) of the elongated guide 730 once the patient has been sedated. In some such alternative embodiment, the oxygen inflow tube 750 and the secondary tube 760 are attached to the elongated guide 730 such that the forward movement of the elongated guide 730 does not interfere with the oxygen inflow tube 750 or the secondary tube 760. In addition, the placement of the oxygen inflow tube 750 and the secondary tube 760 is further configured to keep the elongated guide 730 tethered to the body 712.

The attachment groove 735 is dimensioned to preclude the end of the elongated guide 730 from entering the central passageway 714. While it is shown in FIGS. 7A and 7B that the attachment groove 735 of the elongate guide 730 snaps into place at a cutaway of the body 712 (e.g., an exact fit), various other attachment mechanisms are also contemplated. As an exemplary alternative, the attachment groove 735 is slightly wider than the cutaway of the body 712, so the elongated guide 730 does not fall back into the mouth of the patient if the attachment groove 735 is not snapped completely into place. As another exemplary alternative, the body 712 does not include a cutaway. The attachment groove 735 of the elongate guide 730 flares out and is dimensioned to sit at an edge of the body 712 without going through the central passageway 714.

While various examples of the present disclosure have been described above, it should be understood that they have been presented by way of example only, and not limitation. Numerous changes to the disclosed examples can be made in accordance with the disclosure herein without departing from the spirit or scope of the invention. Thus, the breadth and scope of the present invention should not be limited by any of the above described examples. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. An endoscopic bite block, comprising:
a base having a body and a central passageway extending through the body, the central passageway extending between teeth and into a mouth of a patient when the body is encapsulated by lips of the patient, the central passageway configured to receive an endoscope;
an elongated guide having a longitudinal curvature corresponding in shape to an oral-pharyngeal cavity of the patient, the elongated guide protruding from the base toward a retropharyngeal space of the patient, the elongated guide having a lateral curvature for guiding the endoscope along the longitudinal curvature of the elongated guide;
a flange at an end of the base opposite the elongated guide, the flange having a first opening, a second opening, and a central opening disposed between the first opening and the second opening;
an oxygen inflow tube configured to receive oxygen gas from an oxygen source; and
a secondary tube configured to receive gas from a gas source,
wherein the oxygen inflow tube and the secondary tube are configured to be introduced through the same opening of the first and second openings of the flange and extend from the base along opposite sides of the elongated guide.

2. The endoscopic bite block of claim 1, wherein the base includes a recess configured to engage upper and lower teeth of the patient during an endoscopic procedure.

3. The endoscopic bite block of claim 1, wherein the elongated guide is configured to depress a tongue of the patient upon insertion thereby displacing an epiglottis away from a posterior pharyngeal wall of the patient.

4. The endoscopic bite block of claim 1, wherein the oxygen inflow tube is integral to the elongated guide such that the oxygen inflow tube follows the longitudinal curvature of the elongated guide.

5. The endoscopic bite block of claim 4, wherein the elongated guide is further configured to guide the oxygen inflow tube to a retropharyngeal space of the patient.

6. The endoscopic bite block of claim 4, wherein the secondary tube comprises a second oxygen inflow tube, and the second oxygen inflow tube is integral to the elongated guide.

7. The endoscopic bite block of claim 1, wherein the secondary tube comprises an end-tidal carbon dioxide return tube for monitoring carbon dioxide in respiratory gases of the patient.

8. The endoscopic bite block of claim 7, wherein the end-tidal carbon dioxide return tube is attached to or integrated to the base.

9. The endoscopic bite block of claim 1, wherein the elongated guide includes a first side and a second side opposite the first side, the first side is configured to contact the tongue of the patient, and the second side is configured to contact palate tissue of the patient, and
wherein the elongated guide is further configured to guide the endoscope along the first side of the elongated guide, and the oxygen inflow tube is configured to extend along the second side of the elongated guide opposite the first side of the elongated guide.

10. The endoscopic bite block of claim 1, further comprising a detachable elastic headband for holding the base in place relative to the oral cavity of the patient.

11. The endoscopic bite block of claim 1, wherein the flange is dimensioned to preclude the end from entering the oral cavity of the patient.

12. The endoscopic bite block of claim 1, wherein the elongated guide includes a flexible distal portion configured to flex in an anterior direction.

13. An endoscopic bite block, comprising:
a base having a body including a recess configured to engage upper and lower teeth of a patient, the base having a central passageway extending through the body, the central passageway extending between the upper and lower teeth and into a mouth of the patient when the body is encapsulated by lips of the patient, the central passageway configured to receive an endoscope;
an elongated guide having a longitudinal curvature corresponding in shape to an oral-pharyngeal cavity of the patient, the elongated guide protruding from the base toward a retropharyngeal space of the patient, the elongated guide having a lateral curvature for guiding the endoscope along the longitudinal curvature of the elongated guide;
a flange at an end of the base opposite the elongated guide, the flange having a first opening, a second opening, and a central opening disposed between the first opening and the second opening;
an oxygen inflow tube integral to the elongated guide and configured to receive oxygen gas from an oxygen source; and
a secondary tube configured to receive gas from a gas source,
wherein the oxygen inflow tube and the secondary tube are configured to be introduced through the same opening of the first and second openings of the flange and extend from the base along opposite sides of the elongated guide.

14. The endoscopic bite block of claim 13, wherein the secondary tube comprises a second oxygen inflow tube integral to the elongated guide and extending from the base along the longitudinal curvature of the elongated guide.

15. The endoscopic bite block of claim 13, wherein the secondary tube comprises an end-tidal carbon dioxide return tube, wherein the end-tidal carbon dioxide return tube is integral to the elongated guide and extends from the base along the longitudinal curvature of the elongated guide, or wherein the end-tidal carbon dioxide return tube is attached to or integrated to the base.

16. The endoscopic bite block of claim 13, wherein the elongated guide includes a first side and a second side opposite the first side, the first side is configured to contact the tongue of the patient, and the second side is configured to contact palate tissue of the patient, and
wherein the elongated guide is further configured to guide the endoscope along the first side of the elongated guide, and the oxygen inflow tube is configured to extend along the second side of the elongated guide opposite the first side of the elongated guide.

17. The endoscopic bite block of claim 13, wherein the elongated guide includes a flexible distal portion configured to flex in an anterior direction.

18. An endoscopic bite block kit, comprising:

an endoscopic bite block having a base, an elongated guide, a flange, an oxygen inflow tube, and a secondary tube, wherein:

the base includes a body and a central passageway extending through the body, the central passageway extending between teeth and into a mouth of a patient when the body is encapsulated by lips of the patient, the body having a recess configured to engage the teeth of the patient, the central passageway configured to receive an endoscope, the elongated guide includes a longitudinal curvature corresponding in shape to an oral-pharyngeal cavity of the patient, the elongated guide protrudes from the base toward a retropharyngeal space of the patient, the elongated guide includes a lateral curvature for guiding the endoscope along the longitudinal curvature of the elongated guide, the flange, positioned at an end of the base opposite the elongated guide, has a first opening, a second opening, and a central opening disposed between the first opening and the second opening, the oxygen inflow tube is integral to the elongated guide and is configured to receive oxygen gas from an oxygen source, the secondary tube is configured to receive gas from a gas source, and the oxygen inflow tube and the secondary tube are configured to be introduced through the same opening of the first and second openings of the flange and extend from the base along opposite sides of the elongated guide;
and a gas tube configured to couple to at least the oxygen inflow tube or the secondary tube of the endoscopic bite block at a first end of the gas tube and configured to couple to at least the oxygen source or the gas source at a second end of the gas tube.

19. The endoscopic bite block kit of claim 18, further comprising an elastic headband for holding the base of the endoscopic bite block in place relative to the oral cavity of the patient, the elastic headband configured to attach to the endoscopic bite block.

20. The endoscopic bite block kit of claim 18, wherein the endoscopic bite block is disposable.

21. The endoscopic bite block kit of claim 18, wherein the secondary tube comprises an end-tidal carbon dioxide return tube for monitoring carbon dioxide in respiratory gases of the patient, and wherein the end-tidal carbon dioxide return tube is attached to or integrated to the base.

22. The endoscopic bite block kit of claim 18, wherein the secondary tube comprises a second oxygen inflow tube integral to the elongated guide and extending from the base along the longitudinal curvature of the elongated guide.

23. An endoscopic bite block, comprising:

a base having a body and a flange, a central passageway extending through the body, the body configured to be encapsulated by lips of a patient thereby keeping a mouth of the patient open during a medical procedure, the central passageway extending between teeth and into the mouth when the body is encapsulated by the lips, the central passageway configured to receive an endoscope, the flange dimensioned to preclude the flange from entering an oral cavity of the patient;

an oxygen inflow tube protruding from the base and configured to receive oxygen gas from an oxygen source;

a secondary tube configured to receive gas from a gas source; and an elongated guide protruding from the base, wherein the elongated guide is configured to guide the oxygen inflow tube to a retropharyngeal space of the patient, wherein:

the flange having a first opening, a second opening, and a central opening disposed between the first opening and the second opening, the oxygen inflow tube protrudes from the base in a same direction as the elongated guide, the oxygen inflow tube is configured to supply the received oxygen gas to the retropharyngeal space of the patient, the oxygen inflow tube and the secondary tube are configured to be introduced through the same opening of the first and second openings of the flange and extend from the base along opposite sides of the elongated guide, and the elongated guide includes a longitudinal curvature corresponding in shape to an oral-pharyngeal cavity of the patient and a lateral curvature for guiding a medical device along the longitudinal curvature, thereby protecting a throat passageway of the patient.

24. The endoscopic bite block of claim 23, wherein the oxygen inflow tube protrudes from the base in the same longitudinal curvature as the elongated guide.

25. The endoscopic bite block of claim 23, wherein the secondary tube comprises a second oxygen inflow tube integral to the elongated guide and extending from the base along the longitudinal curvature of the elongated guide or an end-tidal carbon dioxide return tube attached to or integrated to the base.

\* \* \* \* \*